(12) United States Patent
Sugiyama et al.

(10) Patent No.: US 12,059,209 B2
(45) Date of Patent: Aug. 13, 2024

(54) OPTICAL COHERENCE TOMOGRAPHIC DEVICE AND NON-TRANSITORY COMPUTER-READABLE RECORDING MEDIUM STORING COMPUTER-READABLE INSTRUCTIONS FOR OPTICAL COHERENCE TOMOGRAPHIC DEVICE

(71) Applicant: Tomey Corporation, Nagoya (JP)

(72) Inventors: Satoshi Sugiyama, Nagoya (JP); Kota Totani, Nagoya (JP); Nobuyori Aoki, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 467 days.

(21) Appl. No.: 17/471,460

(22) Filed: Sep. 10, 2021

(65) Prior Publication Data

US 2022/0079435 A1    Mar. 17, 2022

(30) Foreign Application Priority Data

Sep. 11, 2020   (JP) ................................ 2020-153095

(51) Int. Cl.
*A61B 3/12*   (2006.01)
*A61B 3/00*   (2006.01)
*A61B 3/10*   (2006.01)

(52) U.S. Cl.
CPC .......... *A61B 3/1241* (2013.01); *A61B 3/0058* (2013.01); *A61B 3/102* (2013.01); *A61B 3/1233* (2013.01)

(58) Field of Classification Search
CPC ..... A61B 3/1241; A61B 3/0058; A61B 3/102; A61B 3/1233; A61B 3/1225
See application file for complete search history.

(56) References Cited

U.S. PATENT DOCUMENTS

2013/0188133 A1   7/2013   Iwase et al.
2014/0121506 A1   5/2014   Iwase et al.
(Continued)

FOREIGN PATENT DOCUMENTS

| JP | 2013-146445 A | 8/2013 |
|---|---|---|
| JP | 2016-057197 A | 4/2016 |

(Continued)

*Primary Examiner* — James C. Jones
(74) *Attorney, Agent, or Firm* — Shumaker, Loop & Kendrick, LLP

(57) ABSTRACT

An optical coherence tomographic device of polarization-sensitive type may include: an image capturing unit configured to capture a tomographic image of a subject eye, and a display unit configured to display the tomographic image captured by the image capturing unit. The tomographic image may include at least two images selected from a group consisting of: an image showing a tissue in the subject eye by scattering intensity, an image showing a melanin distribution in the subject eye, an image showing a fiber density in the subject eye, an image showing a fiber direction in the subject eye, and an image showing a blood flow in the subject eye. The display unit may be configured to display the at least two images at a same position and on a same cross section such that the at least two images are superimposed on each other.

8 Claims, 12 Drawing Sheets
(6 of 12 Drawing Sheet(s) Filed in Color)

(56) References Cited

U.S. PATENT DOCUMENTS

| | | |
|---|---|---|
| 2016/0069664 A1 | 3/2016 | Yamanari |
| 2016/0100756 A1 | 4/2016 | Iwase et al. |
| 2017/0256054 A1 | 9/2017 | Matsumura et al. |
| 2017/0316567 A1 | 11/2017 | Kotoku et al. |
| 2018/0035894 A1 | 2/2018 | Yamanari |
| 2018/0232914 A1* | 8/2018 | Sumiya .................... G06T 7/11 |

FOREIGN PATENT DOCUMENTS

| | | |
|---|---|---|
| JP | 6146951 B2 | 6/2017 |
| JP | 2017153748 A | 9/2017 |
| JP | 2017153825 A | 9/2017 |
| JP | 207196306 A | 11/2017 |

* cited by examiner

OPTICAL COHERENCE TOMOGRAPHIC DEVICE AND NON-TRANSITORY COMPUTER-READABLE RECORDING MEDIUM STORING COMPUTER-READABLE INSTRUCTIONS FOR OPTICAL COHERENCE TOMOGRAPHIC DEVICE

CROSS REFERENCE

This application claims priority to Japanese Patent Application No. 2020-153095, filed on Sep. 11, 2020, the entire contents of which are incorporated herein by reference.

TECHNICAL FIELD

Techniques disclosed herein relate to an optical coherence tomographic device of polarization-sensitive type and a non-transitory computer-readable recording medium storing computer-readable instructions for optical coherence tomographic device.

BACKGROUND

Optical coherence tomographic devices have been widely used in ophthalmic devices etc., as a means to obtain tomographic images of living organism's tissues because of their non-invasive and non-contact natures. Further, for optical coherence tomographic devices, techniques have been developed not only to capture tomographic images that show scattering intensities of living organism's tissues but also to capture tomographic images that visualize various types of information of the living organism's tissues. For example, Japanese Patent Application Publication No. 2013-146445 describes an optical coherence tomographic device of polarization-sensitive type. The optical coherence tomographic device of Japanese Patent Application Publication No. 2013-146445 obtains a luminance tomographic image based on the intensity of light returned from a subject eye, as well as a retardation image and a DOPU image showing the polarization state of the subject eye. Further, in the optical coherence tomographic device of Japanese Patent Application Publication No. 2013-146445, the obtained tomographic image based on the intensity of light returned from the subject eye and tomographic image showing the polarization state of the subject eye are displayed in parallel on a display unit. The simultaneous display of plural tomographic images having various characteristics on the display unit facilitates assessment on the subject eye condition from various perspectives.

SUMMARY

In the optical coherence tomographic device of Japanese Patent Application Publication No. 2013-146445, the tomographic image based on the intensity of light returned from the subject eye and the tomographic image showing the polarization state of the same subject eye are displayed in parallel. However, even when the two images are displayed on the same screen, an abnormality etc., in the subject eye is shown in one of the images but this abnormality may not be shown in the other image. For this reason, even though the plural different images of the subject eye are displayed, a user is required to pay attention to the both images and it is difficult to assess the subject eye condition from various perspectives.

The disclosure herein discloses techniques that make it possible to easily grasp a subject eye condition from various perspectives.

An optical coherence tomographic device disclosed herein may be an optical coherence tomographic device of polarization-sensitive type. The optical coherence tomographic device may comprise: an image capturing unit configured to capture a tomographic image of a subject eye; and a display unit configured to display the tomographic image captured by the image capturing unit. The tomographic image may comprise at least two images selected from a group consisting of: an image showing a tissue in the subject eye by scattering intensity, an image showing a melanin distribution in the subject eye, an image showing a fiber density in the subject eye, an image showing a fiber direction in the subject eye, and an image showing a blood flow in the subject eye. The display unit may be configured to display the at least two images at a same position and on a same cross section such that the at least two images are superimposed on each other.

Further, the disclosure herein discloses a non-transitory computer-readable recording medium storing computer-readable instructions for an optical coherence tomographic device. The computer-readable instructions, when executed by a processor of the optical coherence tomographic device, may cause the optical coherence tomographic device to: create at least two tomographic images selected from a group consisting of: a tomographic image showing a tissue in the subject eye by scattering intensity, a tomographic image showing a melanin distribution in the subject eye, a tomographic image showing a fiber density in the subject eye, a tomographic image showing a fiber direction in the subject eye, and a tomographic image showing a blood flow in the subject eye; and display the at least two tomographic images at a same position and on a same cross section such that the at least two tomographic images are superimposed on each other.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
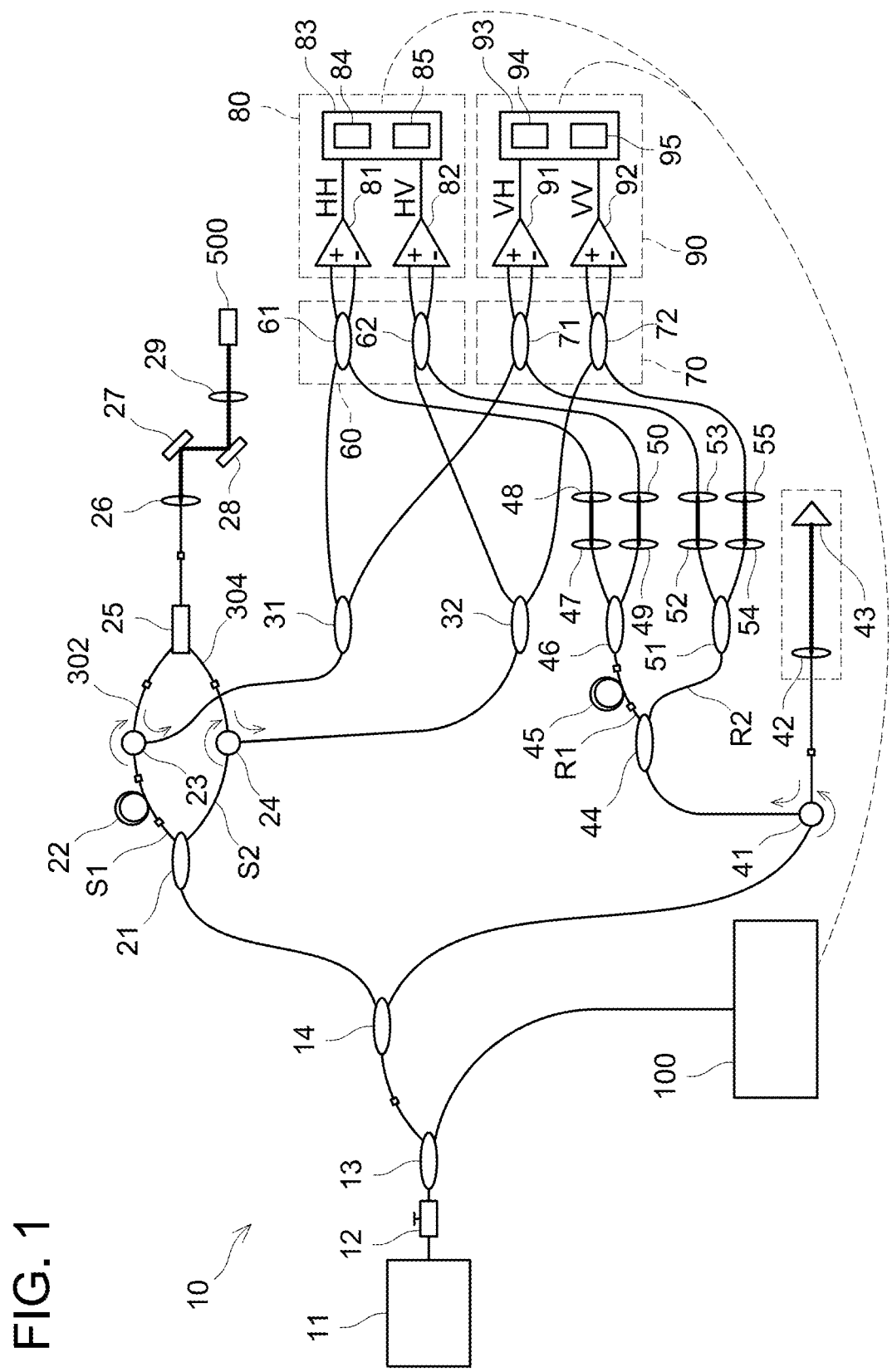
FIG. 1 illustrates a schematic configuration of an optical system in an optical coherence tomographic device according to an embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved optical coherence tomographic devices of polarization-sensitive type, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

An optical coherence tomographic device disclosed herein may be an optical coherence tomographic device of polarization-sensitive type. The optical coherence tomographic device may comprise: an image capturing unit configured to capture a tomographic image of a subject eye; and a display unit configured to display the tomographic image captured by the image capturing unit. The tomographic image may comprise at least two images selected from a group consisting of: an image showing a tissue in the subject eye by scattering intensity, an image showing a melanin distribution in the subject eye, an image showing a fiber density in the subject eye, an image showing a fiber direction in the subject eye, and an image showing a blood flow in the subject eye. The display unit may be configured to display the at least two images at a same position and on a same cross section such that the at least two images are superimposed on each other.

The above optical coherence tomographic device displays the at least two tomographic images that visualize different information of a tissue in the subject eye such that they are superimposed on each other. Therefore, at each position (cross section) of the tissue in the subject eye, the condition can easily be grasped from various perspectives based on the multiple information. Consequently, it is likely to prevent an oversight of a distinguishing feature (finding), such as an ailment, shown in the tomographic images.

The optical coherence tomographic device disclosed herein may further comprise an input device for input of a numerical range of an index to be displayed for each of the at least two images. The display unit may be configured to display each of the at least two images according to the numerical range inputted through the input device. According to such a configuration, it is possible to select index numerical ranges for the images to be displayed according to assessment characteristics desired by a user.

In the optical coherence tomographic device disclosed herein, the input device may be further for input of an order in which the at least two images are superimposed. The display unit may be configured to display the at least two images such that the at least two images are superimposed on each other in the order inputted through the input device. According to such a configuration, it is possible to select a positional relationship of the at least two images (which image is superimposed on top of which image) in superimposing the images according to assessment characteristics desired by the user.

In the optical coherence tomographic device disclosed herein, the image showing a melanin distribution in the subject eye may be created based on entropy. The image showing a fiber density in the subject eye may be created based on birefringence. According to such a configuration, it is possible to create the image showing a melanin distribution in the subject eye and the image showing a fiber density in the subject eye that are suitable for easily grasping the condition of the subject eye.

In the optical coherence tomographic device disclosed herein, the image capturing unit may comprise: a light source; a measurement optical system configured to generate measurement light from light outputted from the light source and to generate reflected light from the subject eye by irradiating the subject eye with the generated measurement light; a reference optical system configured to generate reference light from the light outputted from the light source; and an interference light detector configured to detect interference light, the interference light being a combination of the reflected light from the subject eye generated by the measurement optical system and the reference light generated by the reference optical system. The measurement optical system may be configured to: generate first polarization measurement light and second polarization measurement light from the light outputted from the light source, wherein the first polarization measurement light vibrates in a first direction and the second polarization measurement light vibrates in a second direction different from the first direction; irradiate the subject eye with the first polarization measurement light and the second polarization measurement light; generate first polarization reflected light and second polarization reflected light from reflected light of the first polarization measurement light from the subject eye, wherein the first polarization reflected light vibrates in the first direction and the second polarization reflected light vibrates in the second direction; and generate third polarization reflected light and fourth polarization reflected light from reflected light of the second polarization measurement light from the subject eye, wherein the third polarization reflected light vibrates in the first direction and the fourth polarization reflected light vibrates in the second direction. The interference light detector may be configured to detect first interference light, second interference light, third interference light, and fourth interference light, wherein the first interference light is a combination of the first polarization reflected light and the reference light, the second interference light is a combination of the second polarization reflected light and the reference light, the third interference light is a combination of the third polarization reflected light and the reference light, and the fourth interference light is a combination of the fourth polarization reflected light and the reference light. According to such a configuration, it is possible to suitably create tomographic images that visualize various different information of a tissue in the subject eye (e.g., the image showing the tissue in the subject eye by scattering intensity, the image showing a melanin distribution in the subject eye, the image showing a fiber density in the subject eye, the image showing a fiber direction in the subject eye, etc.).

In the optical coherence tomographic device disclosed herein, the image showing a tissue in the subject eye by scattering intensity may be created by using at least one of the first interference light, the second interference light, the third interference light, and the fourth interference light. Each of the image showing a melanin distribution in the subject eye, the image showing a fiber density in the subject eye, the image showing a fiber direction in the subject eye, and the image showing a blood flow in the subject eye may be created by using the first interference light, the second interference light, the third interference light, and the fourth interference light. According to such a configuration, it is possible to suitably create the image showing the tissue in the subject eye by scattering intensity, the image showing a melanin distribution in the subject eye, the image showing a fiber density in the subject eye, the image showing a fiber direction in the subject eye, and the image showing a blood flow in the subject eye.

In the optical coherence tomographic device disclosed herein, the display unit may be configured to display en-face images of the at least two images created from the tomographic image captured by the image capturing unit. The display unit may be configured to display the en-face images of the at least two images such that the en-face images are superimposed on each other. According to such a configuration, it is possible to easily check the subject eye over a wider range.

Embodiments

First Embodiment

Hereinafter, an optical coherence tomographic device according to the present embodiment will be described. The optical coherence tomographic device according to the present embodiment is a polarization-sensitive OCT (PS-OCT) that is capable of capturing polarization characteristics of a subject to be examined by a Fourier domain method of a wavelength sweeping type using a light source of a wavelength sweeping type (swept-source optical coherence tomography: SS-OCT).

As illustrated in FIG. 1, the optical coherence tomographic device according to the present embodiment comprises a light source 11; a measurement optical system (21 to 29, 31, 32) that generates a measurement light from light outputted from the light source 11; a reference optical system (41 to 46, 51) that generates reference light from the light outputted from the light source 11; interference optical systems 60, 70 that combine reflected light from a subject eye 500 generated in the measurement optical system with the reference light generated in the reference optical system to generate interference light; and interference light detectors 80, 90 that detect the interference light generated in the interference optical system 60, 70.

Light Source

The light source 11 is a light source of a wavelength sweeping type, and the wavelength (wavenumber) of output light varies with a predetermined cycle. Since the wavelength of light with which the subject eye 500 is irradiated varies (sweeps), an intensity distribution of light reflected from depthwise portions of the subject eye 500 can be obtained by subjecting a signal obtained from interference light, which is a combination of the reflected light from the subject eye 500 and the reference light, to Fourier analysis.

A polarization control device 12 and a fiber coupler 13 are connected to the light source 11, and a PMFC (polarization maintaining fiber coupler) 14 and a sampling trigger/clock generator 100 are connected to the fiber coupler 13. Therefore, the light outputted from the light source 11 is inputted to the PMFC 14 and the sampling trigger/clock generator 100 through the polarization control device 12 and the fiber coupler 13. The sampling trigger/clock generator 100 generates a sampling trigger and a sampling clock for each of signal processors 83 and 93 (which will be described later) by using the light from the light source 11.

Measurement Optical System

The measurement optical system (21 to 29, 31, 32) comprises a PMFC 21 connected to the PMFC 14; two measurement light paths S1 and S2 branching off from the PMFC 21; a polarization beam combiner/splitter 25 connecting the two measurement light paths S1 and S2; a collimator lens 26 connected to the polarization beam combiner/splitter 25; galvanometer mirrors 27 and 28; and a lens 29. An optical path length difference generator 22 and a circulator 23 are disposed on the measurement light path S1. Only a circulator 24 is disposed on the measurement light path S2. Therefore, an optical path length difference ΔL between the measurement light path S1 and the measurement light path S2 is generated by the optical path length difference generator 22. The optical path length difference ΔL may be set to be longer than a depthwise measurement range of the subject eye 500. This prevents interference light with different optical path lengths from overlapping each other. As the optical path length difference generator 22, for example, an optical fiber may be used or an optical system such as a mirror, a prism, etc. may be used. In the present embodiment, a PM fiber with a length of one meter is used as the optical path length difference generator 22. The measurement optical system further comprises PMFCs 31, 32. The PMFC 31 is connected to the circulator 23. The PMFC 32 is connected to the circulator 24.

One of light (i.e., measurement light) split by the PMFC 14 is inputted to the measurement optical system (21 to 29, 31, 32). The PMFC 21 splits the measurement light inputted from the PMFC 14 into first measurement light and second measurement light. The first measurement light split by the PMFC 21 is guided to the measurement light path S1, and the second measurement light split by the PMFC 21 is guided to the measurement light path S2. The first measurement light guided to the measurement light path S1 is inputted to the polarization beam combiner/splitter 25 through the optical path length difference generator 22 and the circulator 23. The second measurement light guided to the measurement light path S2 is inputted to the polarization beam combiner/splitter 25 through the circulator 24. A PM fiber 304 is connected to the polarization beam combiner/splitter 25 such that the PM fiber 304 is circumferentially turned by 90 degrees relative to a PM fiber 302. For this reason, the second measurement light inputted to the polarization beam combiner/splitter 25 has a polarization component orthogonal to the first measurement light. Since the optical path length difference generator 22 is disposed on the measurement light path S1, the first measurement light is delayed relative to the second measurement light by a distance corresponding to the optical path length difference generator 22 (that is, the optical path length difference ΔL is generated). The polarization beam combiner/splitter 25 superimposes the inputted first measurement light and second measurement light. The light outputted from the polarization beam combiner/splitter 25 (superimposed light of the first measurement light and the second measurement light) passes through the collimator lens 26, the galvanometer mirrors 27 and 28, and the lens 29 and is then inputted to the subject eye 500. The light inputted to the subject eye 500 is scanned along an x-y direction by the galvanometer mirrors 27 and 28.

The light inputted to the subject eye 500 is reflected by the subject eye 500. The reflected light by the subject eye 500 scatters at the surface of the subject eye 500 and the inside thereof. The reflected light from the subject eye 500 passes through, in the reverse order to the incidence path, the lens 29, the galvanometer mirrors 28, 27, and the collimator lens 26, and is then inputted to the polarization beam combiner/splitter 25. The polarization beam combiner/splitter 25 splits the inputted reflected light into two polarization components that are orthogonal to each other. These are termed horizontal polarization reflected light (horizontal polarization component) and vertical polarization reflected light (vertical polarization component), for convenience sake. The horizontal polarization reflected light is guided to the measurement light path S1, and the vertical polarization reflected light is guided to the measurement light path S2.

The optical path of the horizontal polarization reflected light is changed by the circulator 23, and the horizontal polarization reflected light is inputted to the PMFC 31. The PMFC 31 splits the inputted horizontal polarization reflected light so that it is inputted to each of PMFCs 61, 71. Therefore, the horizontal polarization reflected light inputted to each of the PMFCs 61, 71 contains a reflected light component based on the first measurement light and a reflected light component based on the second measurement light. The optical path of the vertical polarization reflected light is changed by the circulator 24, and the vertical polarization reflected light is inputted to the PMFC 32. The PMFC 32 splits the inputted vertical polarization reflected light so that it is inputted to each of PMFCs 62, 72. Therefore, the vertical polarization reflected light inputted to each of the PMFCs 62, 72 contains a reflected light component based on the first measurement light and a reflected light component based on the second measurement light.

REFERENCE OPTICAL SYSTEM

The reference optical system (41 to 46, 51) comprises a circulator 41 connected to the PMFC 14; a reference delay line (42, 43) connected to the circulator 41; a PMFC 44 connected to the circulator 41; two reference light paths R1 and R2 branching off from the PMFC 44; a PMFC 46 connected to the reference light path R1; and a PMFC 51 connected to the reference light path R2. An optical path length difference generator 45 is disposed on the reference light path R1. No optical path length difference generator is disposed on the reference light path R2. Therefore, an optical path length difference ΔL' between the reference light path R1 and the reference light path R2 is generated by the optical path length difference generator 45. For example, an optical fiber is used as the optical path length difference generator 45. The optical path length difference ΔL' of the optical path length difference generator 45 may be the same as the optical path length difference ΔL of the optical path length difference generator 22. If the optical path length differences ΔL and ΔL' are the same, depthwise positions of a plurality of interference light (described later) in the subject eye 500 coincide with each other. That is, it is unnecessary to align a plurality of acquired tomographic images.

The other of light split by the PMFC 14 (i.e., reference light) is inputted to the reference optical system (41 to 46, 51). The reference light inputted from the PMFC 14 is inputted to the reference delay line (42, 43) through the circulator 41. The reference delay line (42, 43) includes a collimator lens 42 and a reference mirror 43. The reference light inputted to the reference delay line (42, 43) is inputted to the reference mirror 43 through the collimator lens 42. The reference light reflected by the reference mirror 43 is inputted to the circulator 41 through the collimator lens 42. The reference mirror 43 is movable in directions to approach and separate from the collimator lens 42. In the present embodiment, the position of the reference mirror 43 is adjusted before the start of measurement so that a signal from the subject eye 500 will be within an OCT depthwise measurable range.

The optical path of the reference light reflected by the reference mirror 43 is changed by the circulator 41, and the reference light reflected by the reference mirror 43 is inputted to the PMFC 44. The PMFC 44 splits the inputted reference light into first reference light and second reference light. The first reference light is guided to the reference light path R1, and the second reference light is guided to the reference light path R2. The first reference light is inputted to the PMFC 46 through the optical path length difference generator 45. The reference light inputted to the PMFC 46 is split into first split reference light and second split reference light. The first split reference light is inputted to the PMFC 61 through a collimator lens 47 and a lens 48. The second split reference light is inputted to the PMFC 62 through a collimator lens 49 and a lens 50. The second reference light is inputted to the PMFC 51 and then is split into third split reference light and fourth split reference light. The third split reference light is inputted to the PMFC 71 through a collimator lens 52 and a lens 53. The fourth split reference light is inputted to the PMFC 72 through a collimator lens 54 and a lens 55.

Interference Optical System

The interference optical systems 60, 70 include a first interference optical system 60 and a second interference optical system 70. The first interference optical system 60 includes the PMFCs 61 and 62. As described, the horizontal polarization reflected light from the measurement optical system and the first split reference light (light having the optical path length difference ΔL') from the reference optical system are inputted to the PMFC 61. Here, the horizontal polarization reflected light contains a reflected light component (light having the optical path length difference ΔL) based on the first measurement light and a reflected light component (light that does not have the optical path length difference ΔL) based on the second measurement light. Therefore, in the PMFC 61, the first split reference light is combined with the reflected light component (light having the optical path length difference ΔL) based on the first measurement light which is among the horizontal polarization reflected light, as a result of which first interference light (horizontal polarization component) is generated.

The vertical polarization reflected light from the measurement optical system and the second split reference light (light having the optical path length difference ΔL') from the reference optical system are inputted to the PMFC 62. Here, the vertical polarization reflected light contains a reflected light component (light having the optical path length difference ΔL) based on the first measurement light and a reflected light component (light that does not have the optical path length difference ΔL) based on the second measurement light. Therefore, in the PMFC 62, the second split reference light is combined with the reflected light component (light having the optical path length difference ΔL) based on the first measurement light which is among the vertical polarization reflected light, as a result of which second interference light (vertical polarization component) is generated.

The second interference optical system 70 includes the PMFCs 71 and 72. As described, the horizontal polarization reflected light from the measurement optical system and the third split reference light (light that does not have the optical path length difference ΔL') from the reference optical system are inputted to the PMFC 71. Therefore, in the PMFC 71, the third split reference light is combined with a reflected light component (light that does not have the optical path length difference ΔL) based on the second measurement light which is among the horizontal polarization reflected light, as a result of which third interference light (horizontal polarization component) is generated.

The vertical polarization reflected light from the measurement optical system and the fourth split reference light (light that does not have the optical path length difference ΔL') from the reference optical system are inputted to the PMFC 72. Therefore, in the PMFC 72, the fourth split reference light is combined with the reflected light component (light that does not have the optical path length difference ΔL) based on the second measurement light which is among the vertical polarization reflected light, as a result of which fourth interference light (vertical polarization component) is generated. The first interference light and the second interference light correspond to the measurement light that has passed through the measurement light path S1, and the third interference light and the fourth interference light correspond to the measurement light that has passed through the measurement light path S2.

Interference Light Detectors

The interference light detectors 80, 90 include a first interference light detector 80 configured to detect the interference light (the first interference light and the second interference light) generated in the first interference light generator 60, and a second interference light detector 90 configured to detect the interference light (the third interference light and the fourth interference light) generated in the second interference light generator 70.

The first interference light detector 80 comprises balanced light detectors 81 and 82 (which may simply be termed detectors 81, 82 hereinbelow), and a signal processor 83 connected to the detectors 81 and 82. The PMFC 61 is connected to the detector 81, and the signal processor 83 is connected to an output terminal of the detector 81. The PMFC 61 splits the first interference light into two interference light that have phases different from each other by 180 degrees, and inputs the two interference light to the detector 81. The detector 81 performs differential amplification processing and noise reduction processing to the two interference light having phases different from each other by 180 degrees inputted from the PMFC 61 so as to convert them to an electric signal (first interference signal), and outputs the first interference signal to the signal processor 83. That is, the first interference signal is an interference signal HH between the reference light and the horizontal polarization reflected light from the subject eye 500 based on the horizontal polarization measurement light. Similarly, the PMFC 62 is connected to the detector 82, and the signal processor 83 is connected to an output terminal of the detector 82. The PMFC 62 splits the second interference light into two interference light that have phases different from each other by 180 degrees, and inputs the two interference light to the detector 82. The detector 82 performs differential amplification processing and noise reduction processing to the two interference light having phases different from each other by 180 degrees so as to convert them to an electric signal (second interference signal), and outputs the second interference signal to the signal processor 83. That is, the second interference signal is an interference signal HV between the reference light and the vertical polarization reflected light from the subject eye 500 based on the horizontal polarization measurement light.

The signal processor 83 comprises a first signal processing unit 84 to which the first interference signal is inputted, and a second signal processing unit 85 to which the second interference signal is inputted. The first signal processing unit 84 is configured to sample the first interference signal based on a sampling trigger and a sampling clock inputted to the signal processor 83 from the sampling trigger/clock generator 100. The second signal processing unit 85 is configured to sample the second interference signal based on the sampling trigger and the sampling clock inputted to the signal processor 83 from the sampling trigger/clock generator 100. The first and second interference signals sampled in the first signal processing unit 84 and the second signal processing unit 85 are inputted to a processor 202 (which will be described later). A known data acquisition device (a so-called DAQ) may be used as the signal processor 83.

Similar to the first interference light detector 80, the second interference light detector 90 comprises balanced light detectors 91 and 92 (which may simply be termed detectors 91, 92 hereinbelow), and the signal processor 93 connected to the detectors 91 and 92. The PMFC 71 is connected to the detector 91, and the signal processor 93 is connected to an output terminal of the detector 91. The PMFC 71 splits the third interference light into two interference light that have phases different from each other by 180 degrees, and inputs the two interference light to the detector 91. The detector 91 performs differential amplification processing and noise reduction processing to the two interference light having phases different from each other by 180 degrees so as to convert them to an electric signal (third interference signal), and outputs the third interference signal to the signal processor 93. That is, the third interference signal is an interference signal VH between the reference light and the horizontal polarization reflected light from the subject eye 500 based on the vertical polarization measurement light. Similarly, the PMFC 72 is connected to the detector 92, and the signal processor 93 is connected to an output terminal of the detector 92. The PMFC 72 splits the fourth interference light into two interference light that have phases different from each other by 180 degrees, and inputs the two interference light to the detector 92. The detector 92 performs differential amplification processing and noise reduction processing to the two interference light having phases different from each other by 180 degrees so as to convert them to an electric signal (fourth interference signal), and outputs the fourth interference signal to the signal processor 93. That is, the fourth interference signal is an interference signal VV between the reference light and the vertical polarization reflected light from the subject eye 500 based on the vertical polarization measurement light.

The signal processor 93 comprises a third signal processing unit 94 to which the third interference signal is inputted, and a fourth signal processing unit 95 to which the fourth interference signal is inputted. The third signal processing unit 94 is configured to sample the third interference signal based on a sampling trigger and a sampling clock inputted to the signal processor 93 from the sampling trigger/clock generator 100. The fourth signal processing unit 95 is configured to sample the fourth interference signal based on the sampling trigger and the sampling clock inputted to the signal processor 93 from the sampling trigger/clock generator 100. The third and fourth interference signals sampled in the third signal processing unit 94 and the fourth signal processing unit 95 are inputted to the processor 202 (which will be described later). A known data acquisition device (a so-called DAQ) may also be used as the signal processor 93. According to the above configuration, it is possible to acquire the interference signals indicative of four polarization characteristics of the subject eye 500. In the present embodiment, the signal processors 83, 93, each of which comprises two signal processing units, are used, however, different configurations may be employed. For example, one signal processor comprising four signal processing units may be used, or four signal processors each comprising one signal processing unit may be used.

Figure 2:
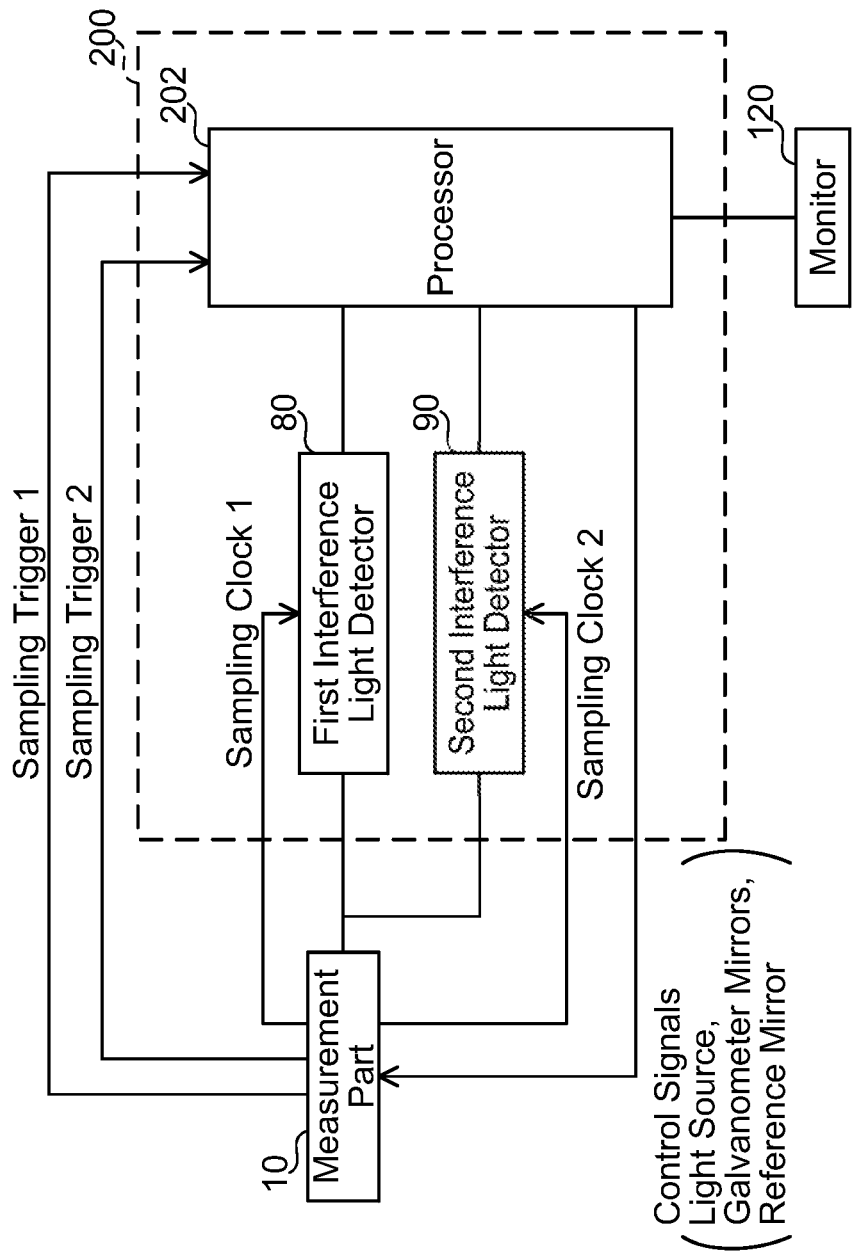
FIG. 2 is a block diagram illustrating a control system of the optical coherence tomographic device according to the embodiment.

Next, the configuration of a control system of the optical coherence tomographic device according to the present embodiment will be described. As illustrated in FIG. 2, the optical coherence tomographic device is controlled by a calculation unit 200. The calculation unit 200 comprises the processor 202, the first interference light detector 80, and the second interference light detector 90. The first interference light detector 80, the second interference light detector 90, and the processor 202 are connected to a measurement unit 10. The processor 202 is configured to output a control signal to the measurement unit 10 to move an incidence position of the measurement light to the subject eye 500 by driving the galvanometer mirrors 27 and 28. The first interference light detector 80 acquires first sampling data with respect to the interference signals (the interference signal HH and the interference signal HV) inputted from the measurement unit 10 based on a sampling clock 1 inputted from the measurement unit 10 and by using a sampling trigger 1 as a trigger, and outputs the first sampling data to the processor 202. The processor 202 performs calculation processing such as Fourier transform, etc. to the first sampling data to generate an HH tomographic image and an HV tomographic image. The second interference light detector 90 acquires second sampling data with respect to the interference signals (the interference signal VH and the interference signal VV) inputted from the measurement unit 10 based on a sampling clock 2 inputted from the measurement unit 10 and by using a sampling trigger 2 as a trigger, and outputs the second sampling data to the processor 202. The processor 202 performs calculation processing such as Fourier transform, etc. to the second sampling data to generate a VH tomographic image and a VV tomographic image. The HH tomographic image, the VH tomographic image, the HV tomographic image, and the VV tomographic image are tomographic images at the same position. Thus, the processor 202 can create tomographic images with four polarization characteristics (HH, HV, VH, VV) that represent a Jones matrix of the subject eye 500.

Figure 3:
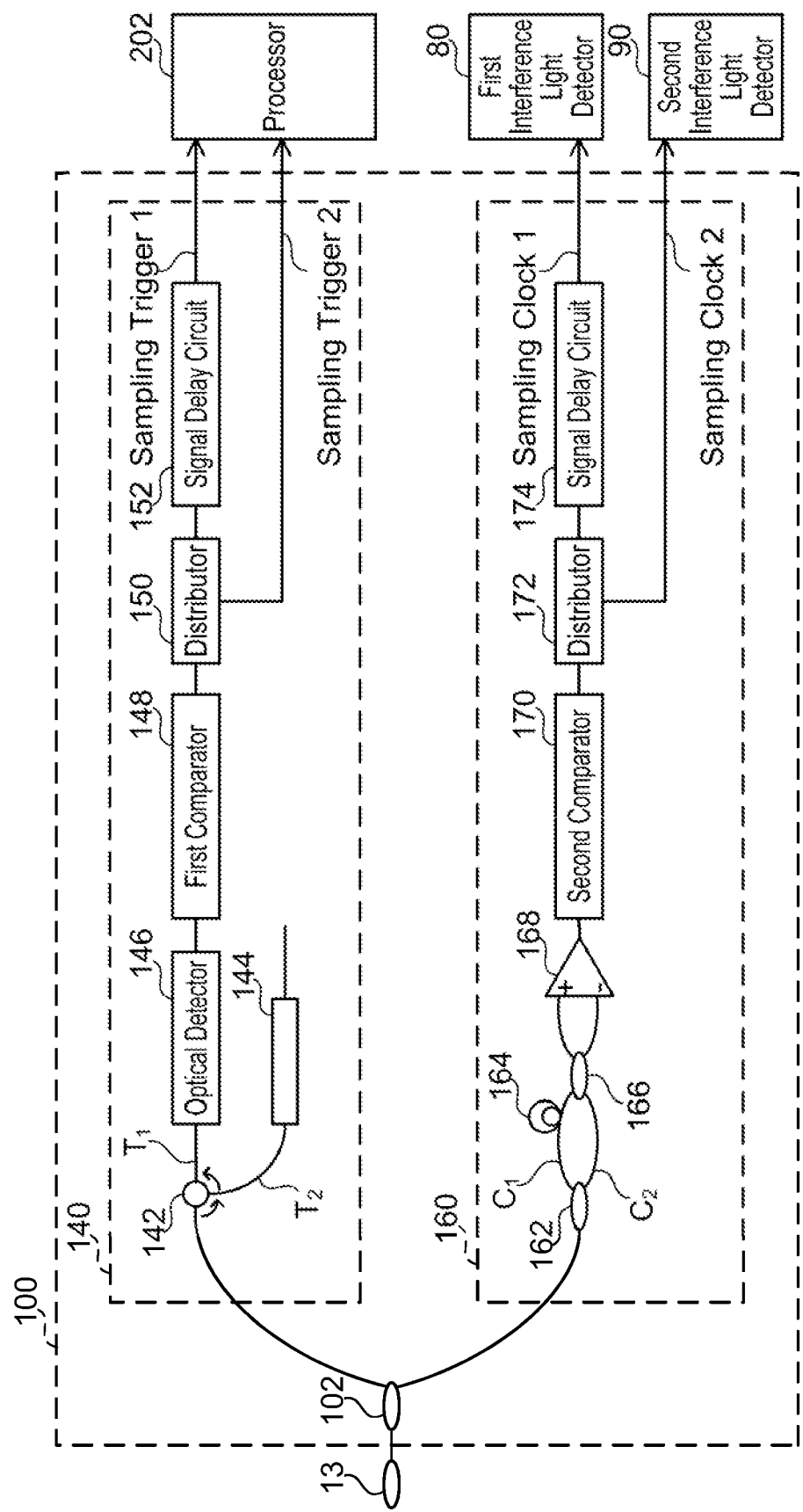
FIG. 3 is a block diagram illustrating a configuration of a sampling trigger/clock generator.

As illustrated in FIG. 3, the sampling trigger/clock generator 100 comprises a fiber coupler 102, a sampling trigger generator (140 to 152), and a sampling clock generator (160 to 174). The light from the light source 11 is inputted, through the fiber coupler 13 and the fiber coupler 102, to each of the sampling trigger generator 140 and the sampling clock generator 160.

Sampling Trigger Generator

The sampling trigger generator 140 may generate a sampling trigger by using, for example, an FBG (fiber bragg grating) 144. As illustrated in FIG. 3, the FBG 144 reflects only a component of the light inputted from the light source 11 that has a specific wavelength, thereby generating a sampling trigger. The generated sampling trigger is inputted to a distributor 150. The distributor 150 distributes the sampling trigger into the sampling trigger 1 and the sampling trigger 2. The sampling trigger 1 is inputted, through a signal delay circuit 152, to the processor 202. The sampling trigger 2 is directly inputted to the processor 202. The sampling trigger 1 is a trigger signal for the interference signals (the first interference signal and the second interference signal) inputted from the first interference light detector 80 to the processor 202. The sampling trigger 2 is a trigger signal for the interference signals (the third interference signal and the fourth interference signal) inputted from the second interference light detector 90 to the processor 202. The signal delay circuit 152 is designed such that the sampling trigger 1 is delayed relative to the sampling trigger 2 by a time corresponding to the optical path length difference ΔL of the optical path length difference generator 22. This makes it possible to make a frequency at which the sampling of the interference signals inputted from the first interference light detector 80 is started equal to a frequency at which the sampling of the interference signals inputted from the second interference light detector 90 is started. Only the sampling trigger 1 may be generated. Since the optical path length difference ΔL is known, the sampling of the interference signals inputted from the second interference light detector 90 may be started such that the start time is delayed from the sampling trigger 1 by a time corresponding to the optical path length difference ΔL.

Sampling Clock Generator

The sampling clock generator may be configured of a Mach-Zehnder interferometer, for example. As illustrated in FIG. 3, the sampling clock generator generates a sampling clock with the same frequency by using the Mach-Zehnder interferometer. The sampling clock generated by the Mach-Zehnder interferometer is inputted to a distributor 172. The distributor 172 distributes the sampling clock into the sampling clock 1 and the sampling clock 2. The sampling clock 1 is inputted, through a signal delay circuit 174, to the first interference light detector 80. The sampling clock 2 is directly inputted to the second interference light detector 90. The signal delay circuit 174 is designed to cause a delay by a time corresponding to the optical path length difference ΔL of the optical path length difference generator 22. This makes it possible to sample interference light with the delay corresponding to the optical path length difference generator 22 at the same timing. Thus, positional misalignment among a plurality of acquired tomographic images can be prevented. In the present embodiment, a Mach-Zehnder interferometer is used to generate the sampling clocks. Alternatively, a Michelson interferometer or an electric circuit may be used to generate the sampling clocks. Alternatively, the sampling clocks may be generated by using a light source including a sampling clock generator.

Next, referring to FIG. 4, a process for displaying tomographic images of the subject eye 500 on a monitor 120 such that they are superimposed on each other will be described. In the present embodiment, a process for displaying tomographic images of the fundus of the subject eye 500 such that they are superimposed on each other is described as an example. It should be noted that tomographic images are not limited to tomographic images of the fundus of the subject eye 500. Tomographic images may be tomographic images of a different part of the subject eye 500 other than the fundus, for example, tomographic images of the anterior eye part.

Figure 4:
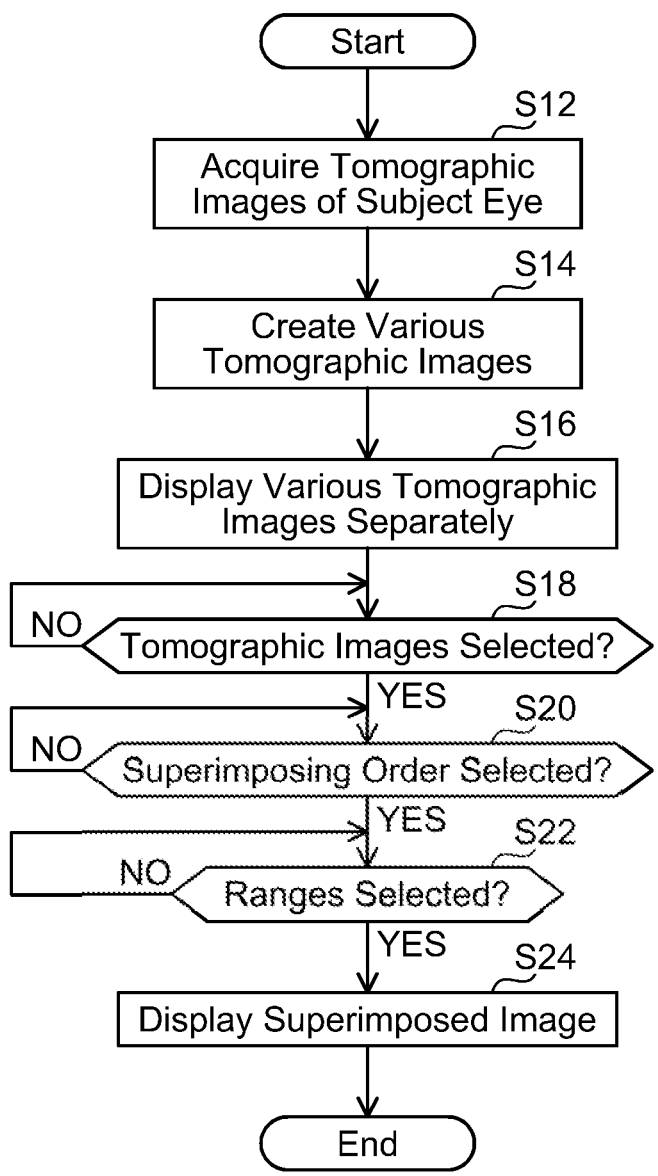
FIG. 4 is a flowchart illustrating an example of a process for displaying tomographic images of a subject eye such that they are superimposed on each other.

As illustrated in FIG. 4, the processor 202 first acquires tomographic images of the subject eye 500 (S12). This acquisition of tomographic images of the subject eye 500 is performed as follows. First, an examiner manipulates a manipulatable member (not illustrated) such as a joystick, etc. to align the optical coherence tomographic device with respect to the subject eye 500. That is, the processor 202 operates a position adjuster (not illustrated) in accordance with the user's manipulation on the manipulatable member. Positions of the optical coherence tomographic device in xy-directions (vertical and horizontal directions) and a z-direction (forward-rearward direction) are thereby adjusted with respect to the subject eye 500.

Then, the processor 202 captures tomographic images of the subject eye 500. In the present embodiment, this capture is performed by raster scanning. In this way, tomographic images for the entirety of the fundus of the subject eye 500 are acquired. Method for capturing tomographic images for the funds of the subject eye 500 is not limited to the raster scanning. It suffices that tomographic images are acquired for the entirety of the fundus of the subject eye 500, and tomographic images may be captured, for example, by radial scanning.

Once acquiring the tomographic images of the fundus of the subject eye 500 in S12, the processor 202 creates various tomographic images indicative of different characteristics from the tomographic images acquired in S12 (S14). Hereinbelow, the description will focus on one of the tomographic images acquired in S12. As described, the optical coherence tomographic device according to the present embodiment can simultaneously acquire a tomographic image captured by inputting a normal wave to the subject eye 500 and a tomographic image captured by inputting a horizontal wave to the subject eye 500, because the optical coherence tomographic device is of polarization-sensitive type. By using these two types of tomographic images, the processor 202 can create not only a tomographic image showing a tissue in the subject eye 500 by scattering intensity (which is a so-called normal tomographic image and may simply be termed "normal tomographic image" hereinbelow), but also a tomographic image showing entropy in the subject eye 500 (which may simply be termed "entropy tomographic image" hereinbelow), a tomographic image showing birefringence in the subject eye 500 (which may simply be termed "birefringence tomographic image" hereinbelow), a tomographic image showing a fiber direction in the subject eye 500 (which may simply be termed "fiber-direction tomographic image" hereinbelow), a tomographic image showing a blood flow in the subject eye 500 (which may simply be termed "blood-flow tomographic image" hereinbelow), etc. In the present embodiment, the normal tomographic image, the entropy tomographic image, the birefringence tomographic image, the fiber-direction tomographic image, and the blood-flow tomographic image are created by using the four interference signals HH, HV, VH, and VV. The normal tomographic image may be created by using at least one of the four interference signals HH, HV, VH, and VV.

The entropy tomographic image, the birefringence tomographic image, the fiber-direction tomographic image, and the blood-flow tomographic image can be created by using known methods. For example, the entropy tomographic image can be created by calculating the entropy of the acquired tomographic image. The birefringence tomographic image can be created as follows. In capturing a tomographic image, scattered light beams caused by microstructures that are smaller than the OCT resolution interfere with each other, thereby generating speckles. Phase differences between signals of polarization of the generated speckles are displayed. In this way, the birefringence tomographic image is created. The fiber-direction tomographic image can be created by calculating a birefringence axis. The blood-flow tomographic image can be created as follows. The capture of a tomographic image is performed multiple times in S12. At this time, scattered light beams caused by microstructures that are smaller than the OCT resolution interfere with each other, thereby generating speckles. A dispersion of scattering intensity signals or phase signals of the generated speckles is displayed. In this way, the blood-flow tomographic image is created. These different types of tomographic images are tomographic images showing the same cross section and position in the subject eye 500. It should be noted that tomographic images to be created may be any types of tomographic images as long as they can be created by using the optical coherence tomographic device of polarization-sensitive type, and tomographic images showing different characteristics from those described above may be created.

Next, the processor 202 displays the various tomographic images created in S14 on the monitor 120 (S16). That is, in the present embodiment, the processor 202 displays the normal tomographic image, the entropy tomographic image, the birefringence tomographic image, the fiber-direction tomographic image, and the blood-flow tomographic image, which were created in S14, in parallel on the monitor 120.

Figure 5:
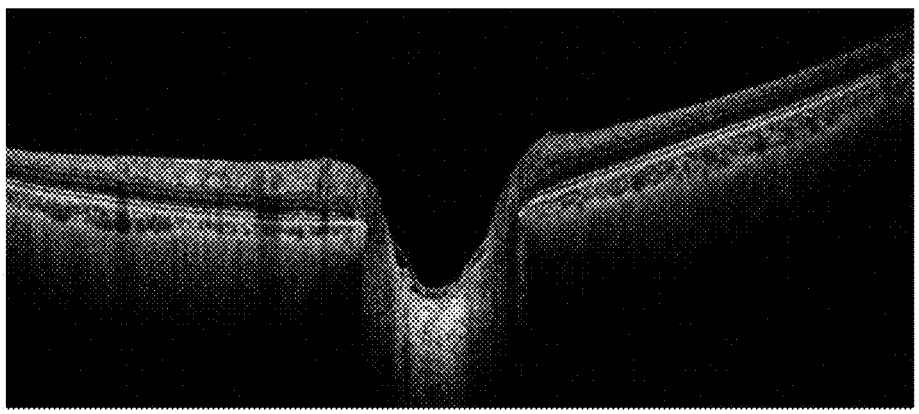
FIG. 5 is an example of how a tomographic image showing a tissue in a subject eye by scattering intensity (so-called normal tomographic image) is displayed alone.
Figure 6:
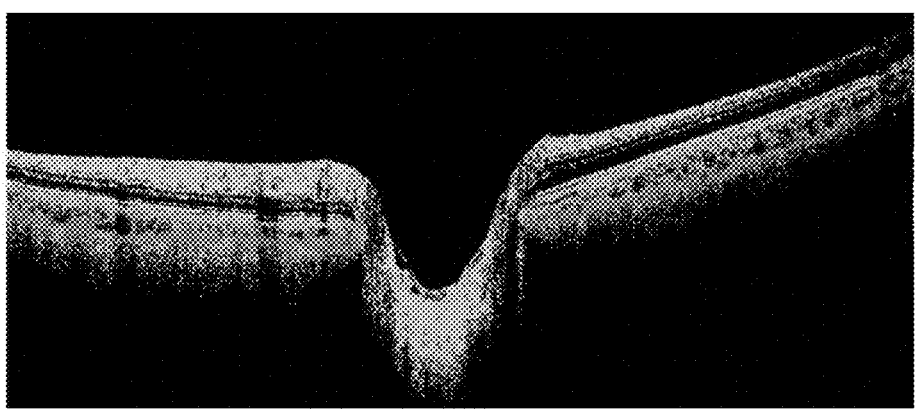
FIG. 6 is an example of how a tomographic image showing entropy in the subject eye is displayed alone.
Figure 7:
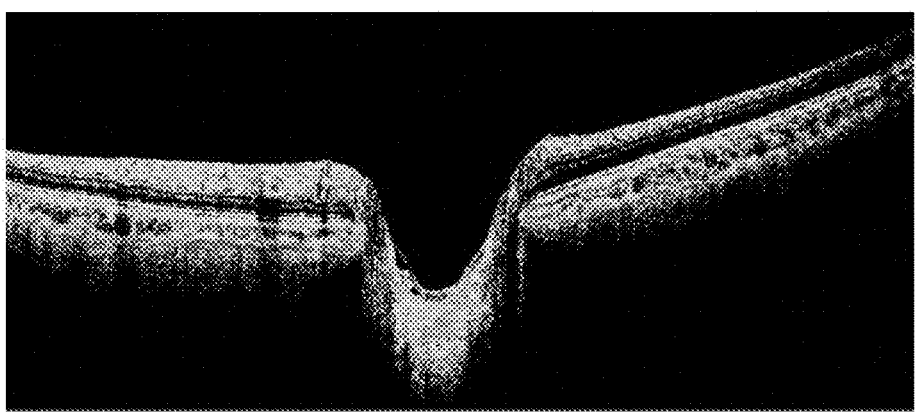
FIG. 7 is an example of how a tomographic image showing birefringence in the subject eye is displayed alone.
Figure 8:
FIG. 8 is an example of how a tomographic image showing a fiber direction in the subject eye is displayed alone.
Figure 9A:
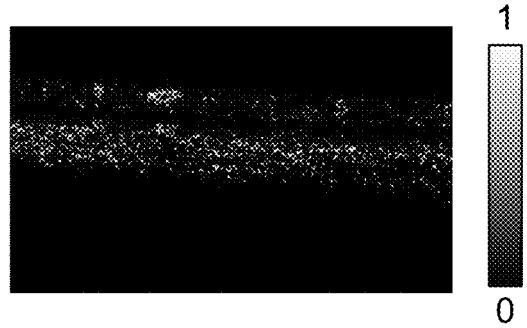
FIG. 9A is an example of how a tomographic image showing a blood flow in the subject eye is displayed alone.
Figure 9B:
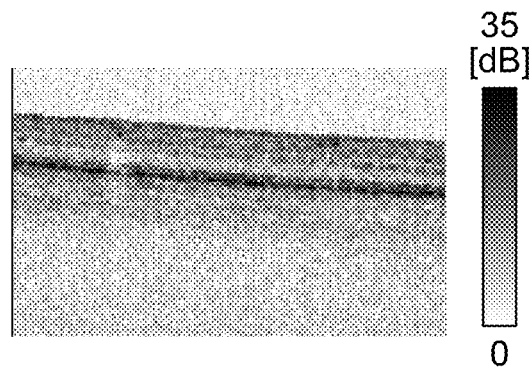
FIG. 9B is a normal tomographic image corresponding to the tomographic image of FIG. 9A.

Each of the tomographic images is displayed with an index suitable for the characteristic shown in the tomographic image. For the normal tomographic image, the index is, for example, scattering intensity (luminance) (dB). In the example of FIG. 5, the tomographic image is displayed in black in areas with 0 dB, displayed in white in areas with 35 dB, and displayed in color gradation in areas between 0 to 35 dB. For the entropy tomographic image, the index is, for example, dimensionless quantity. In the example of FIG. 6, the tomographic image is displayed in yellow in areas with 0, displayed in blue in areas with 1, and displayed in color gradation of yellow, orange, red, purple, and blue in areas between 0 to 1. For the birefringence tomographic image, the index is, for example, phase delay amount (rad) caused by birefringence. In the example of FIG. 7, the tomographic image is displayed in yellow in areas with 0 rad, displayed in dark blue in areas with 0.5 rad, and displayed in color gradation of yellow, greenish yellow, green, blue, and dark blue in areas between 0 to 0.5 rad. For the fiber-direction tomographic image, the index is, for example, angle of birefringence axis (rad). In the example of FIG. 8, the tomographic image is displayed in black in areas with $-\pi$, displayed in white in areas with $+\pi$, and displayed in color gradation in areas between $-\pi$ and $+\pi$. For the blood-flow tomographic image, the index is, for example, dimensionless quantity. In the example of FIG. 9A, the tomographic image is displayed in black in areas with 0, displayed in white in areas with 1, and displayed in color gradation in areas between 0 to 1.

Next, the processor 202 determines whether two or more tomographic images are selected from among the displayed tomographic images (S18). Specifically, the user selects desired images from among the various types of tomographic images displayed on the monitor ¥ 120 by using an input device (not illustrated) such as a mouse, etc. When completing the image selection, the user notifies that the image selection has been completed. For example, the user notifies that the image selection has been completed by pushing a button "Finish" displayed on the monitor 120 with the input device. The processor 202 waits until the completion of the image selection is notified (NO in S18). Hereinbelow, a case where the user has selected the normal tomographic image and the entropy tomographic image will be described as an example.

When the completion of the image selection has been notified (YES in S18), the processor 202 determines whether an order in which the images selected in S18 are to be superimposed (which may be termed "superimposing order" hereinbelow) is selected (S20). Specifically, the user selects a superimposing order for the selected tomographic images displayed on the monitor 120 by using the input device (not illustrated) such as a mouse, etc. Then, when completing the order selection, the user notifies the completion of the order selection. The processor 202 waits until the completion of the order selection is notified (NO in S20). For the normal tomographic image and the entropy tomographic image selected in S18, the user selects a superimposing order, for example, in which the entropy tomographic image is superimposed on top of the normal tomographic image.

When the completion of the order selection has been notified (YES in S20), the processor 202 determines for each of the selected tomographic images whether a numerical range of the index (which may simply be termed "range" hereinbelow) is selected (S22). Specifically, the user selects, for each of the selected tomographic images, a range to be displayed out of the entire range of the index by using the input device (not illustrated) such as a mouse, etc. For example, in the case where the entropy tomographic image is superimposed on top of the normal tomographic image, the user does not select a range for the normal tomographic image in order to display the entire range which is the same as the one displayed in S16, whereas the user selects for the entropy tomographic image, for example, a range of 0.3 to 0.7 out of the dimensionless quantity range of 0 to 1 (entire range) displayed in S16 to exclude values around 0 and 1. When completing the range selection, the user notifies the completion of the range selection. The processor 202 waits until the completion of the range selection is notified (NO in S22).

When the completion of the range selection has been notified (YES in S22), the processor 202 displays the images selected in S18 on the monitor 120 such that they are superimposed on each another (S24). At this time, the processor 202 superimposes the tomographic images on each another according to the order selected in S20 (i.e., which one of the images is superimposed on top of the other image). Further, the processor 202 superimposes the tomographic images showing the ranges selected in S22. For example, in the example of FIG. 10, the processor 202 superimposes the entropy tomographic image on top of the normal tomographic image according to the order selected in S20. At this time, the processor 202 displays, according to the ranges selected in S22, the normal tomographic image showing the entire range and superimposes the entropy tomographic image showing only the range of 0.3 to 0.7 on top of the normal tomographic image.

Figure 10:
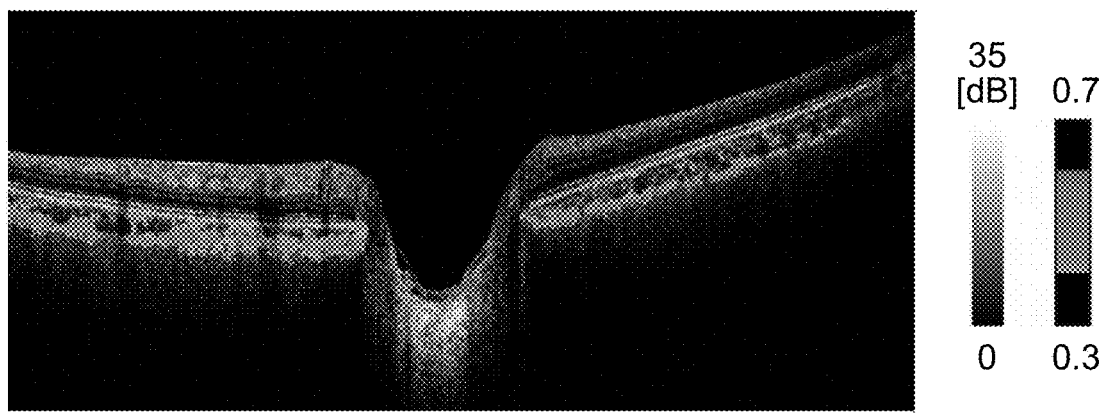
FIG. 10 is an example of an image in which tomographic images are superimposed on each other, where the tomographic image showing entropy in the subject eye is superimposed on the normal tomographic image.

For example, in the example of FIG. 10, the entropy tomographic image is superimposed on top of the normal tomographic image, and an image in which the tomographic images are superimposed as such is displayed on the monitor 120. By displaying calculated entropy, it is possible to visualize a distribution of substance, for example and mainly melanin, in the subject eye 500. The detailed internal structure of the subject eye 500 may not be grasped just by checking the entropy tomographic image, and thus it may be difficult to understand in which part of the subject eye 500 melanin distributes. To the contrary, positions, etc. of tissues in the subject eye 500 can be visually identified in the normal tomographic image. Since the entropy tomographic image is superimposed on top of the normal tomographic image in the example of FIG. 10, the user can check the melanin distribution in the subject eye 500 while grasping the internal structure of the subject eye 500 owing to the normal tomographic image, thereby facilitating the understanding of a correspondence relationship between the internal structure of the subject eye 500 and the melanin distribution. This helps, for example, to find ailments resulting from a change in retinal pigment epithelial cells (RPE cells) and to diagnose age-related macular degeneration and retinitis pigmentosa.

In the example of FIG. 10, the entropy tomographic image is superimposed on top of the normal tomographic image, with the range of 0 to 1 limited to the range of 0.3 to 0.7. Thus, only the range the user is interested in can be displayed.

Figure 11:
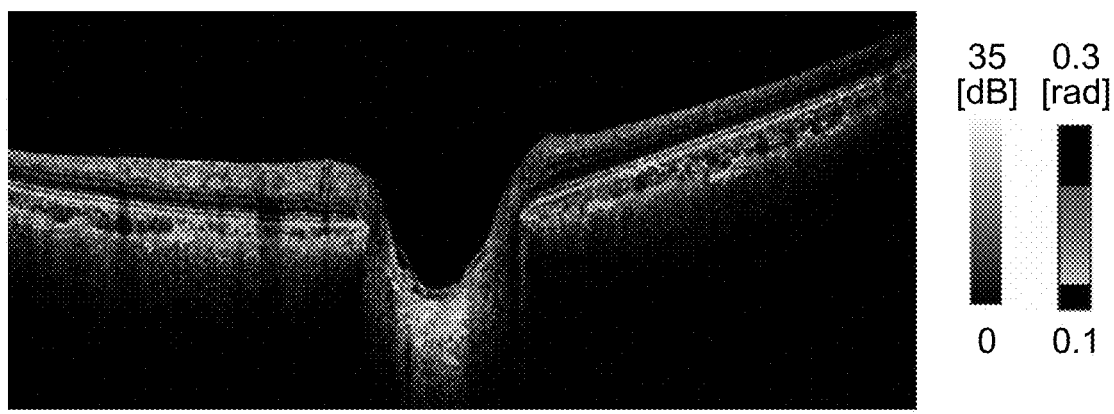
FIG. 11 is another example of an image in which tomographic images are superimposed on each other, where the tomographic image showing birefringence in the subject eye is superimposed on the normal tomographic image.

The above example assumes that the entropy tomographic image is superimposed on top of the normal tomographic image, however, any combination of tomographic images may be superimposed. For example, as illustrated in FIG. 11, the birefringence tomographic image may be superimposed on the normal tomographic image. In the birefringence tomographic image, it is possible to grasp a fiber density distribution in the subject eye 500. Superimposing the birefringence tomographic image on top of the normal tomographic image facilitates the understanding of a correspondence relationship between the internal structure of the subject eye 500 and the fiber density distribution. This helps to find ailments resulting from structural change of the subject eye 500 due to increase in eye axial length and/or high intraocular pressure and to diagnose excessive myopia and glaucoma.

The fiber-direction tomographic image may be superimposed on top of the normal tomographic image. Superimposing the fiber-direction tomographic image on top of the normal tomographic image facilitates the understanding of a correspondence relationship between the internal structure of the subject eye 500 and the fiber direction in the subject eye 500. This helps to find ailments resulting from structural change of the subject eye 500 due to increase in eye axial length and/or high intraocular pressure and to diagnose excessive myopia and glaucoma.

The blood-flow tomographic image may be superimposed on top of the normal tomographic image. Superimposing the blood-flow tomographic image on top of the normal tomographic image facilitates the understanding of a correspondence relationship between the internal structure of the subject eye 500 and a blood flow distribution in the subject eye 500. This helps to find blood vessel abnormalities and to diagnose aliments resulting from ischemia such as glaucoma, myopia, etc. and aliments resulting from abnormal blood vessels such as choroidal neovascular, etc.

In the above examples, two tomographic images are superimposed, however, the number of tomographic images to be superimposed is non-limiting, and three or more tomographic images may be superimposed. Superimposing three or more tomographic images facilitates the understanding of correspondence relationships among different characteristics of the subject eye 500.

Figure 12:
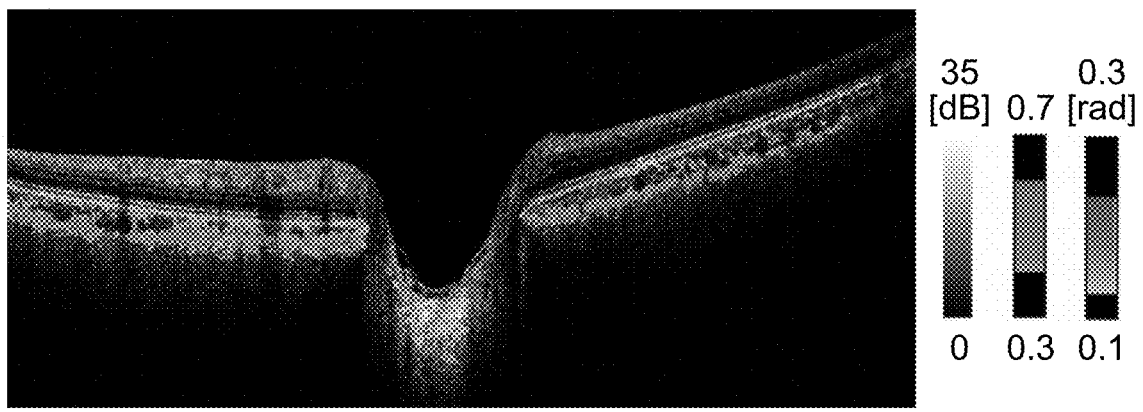
FIG. 12 is yet another example of an image in which tomographic images are superimposed on each other, where the tomographic image showing birefringence in the subject eye is superimposed on the normal tomographic image and the tomographic image showing entropy in the subject eye is further superimposed on the tomographic image showing birefringence in the subject eye.

For example, in the example of FIG. 12, three tomographic images, namely the normal tomographic image, the entropy tomographic image, and the birefringence tomographic image, are superimposed on one another. In this case, the normal tomographic image, the entropy tomographic image, and the birefringence tomographic image are selected in S18. Then, in S20, the processor 202 determines whether a superimposing order of the three tomographic images is selected. For example, the user selects a superimposing order such that the birefringence tomographic image is to be superimposed on top of the normal tomographic image and the entropy tomographic image is to be superimposed on top of the birefringence tomographic image. Then, in S22, the processor 202 determines for each of the three images whether a range to be displayed is selected. For example, the user does not select a range for the normal tomographic image, selects a range of dimensionless quantity 0.3 to 0.7 for the entropy tomographic image, and selects a range of 0.1 to 0.3 rad out of the entire phase delay amount range of 0 to 0.5 rad for the birefringence tomographic image. Then, in S24, the processor 202 displays the three tomographic images on the monitor 120 such that they are superimposed on one another. At this time, the processor 202 superimposes the normal tomographic image, the birefringence tomographic image, and the entropy tomographic image according to the order selected in S20. At this time, the processor 202 displays, according to the ranges selected in S22, the entire range of the normal tomographic image, superimposes the birefringence tomographic image showing only the range of 0.1 to 0.3 rad on top of the normal tomographic image, and further superimposes the entropy tomographic image showing only the range of 0.3 to 0.7 on top of the birefringence tomographic image.

Superimposing the entropy tomographic image and the birefringence tomographic image on the normal tomographic image facilitates the understanding of correspondence relationships between the internal structure of the subject eye 500 and each of the melanin distribution and the fiber density, as well as the understanding of a correspondence relationship between the melanin distribution and the fiber density.

Figure 13:
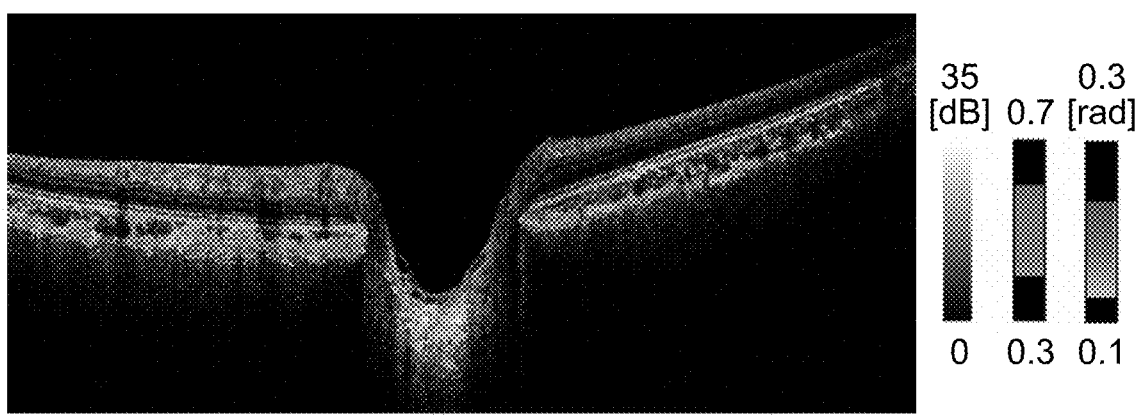
FIG. 13 is yet another example of an image in which tomographic images are superimposed on each other, where the tomographic image showing entropy in the subject eye is superimposed on the normal tomographic image and the tomographic image showing birefringence in the subject eye is further superimposed on the tomographic image showing entropy in the subject eye.

In the present embodiment, tomographic images are superimposed on each other in S24 according to the order selected in S20, however, other configurations may be employed. For example, after tomographic images have been superimposed and displayed in S24, the superimposing order may be changed. When the user changes the superimposing order of the tomographic images after checking the displayed image, an underlying tomographic image can be moved to the superficial side, thereby facilitating the user's understanding of a correspondence relationship between the tomographic images. FIG. 13 illustrates an image in which the entropy tomographic image is superimposed on top of the normal tomographic image and the birefringence tomographic image is superimposed on top of the entropy tomographic image. Although the normal tomographic image, the entropy tomographic image, and the birefringence tomographic image are superimposed in each of FIGS. 12 and 13, the entropy tomographic image is the uppermost tomographic image in FIG. 12, whereas the birefringence tomographic image is the uppermost tomographic image in FIG. 13. By comparing different images in which the same types of tomographic images are superposed on one another in different orders, the user can more clearly understand correspondence relationships of the tomographic images.

In the present embodiment, a range to be displayed is selectable for each tomographic image in S22, however, for example, a color to be used in each tomographic image may be selectable in addition to the range. Specifically, in S22, the processor 202 may determine whether a color to be used in each tomographic image is selected, after a range to be displayed has been selected for each tomographic image. As described, each tomographic image is displayed in color gradation within the index range of the tomographic image. If a color to be used is not selected, the tomographic image is displayed in color gradation within the selected range. This display of tomographic image in color gradation helps the user to understand a numerical value distribution within the selected range for the tomographic image. On the other hand, if a color to be used is selected, the tomographic image is displayed in the selected single color regardless of numerical values. Displaying a tomographic image in a single color provides decreased amount of information on the tomographic image, whereas it makes it clearer which type of tomographic image is displayed. Thus, especially when multiple tomographic images are to be superimposed, for example, when at least two tomographic images are to be superimposed on the normal tomographic image, displaying each tomographic image in a single color helps to distinguish the tomographic images by their colors.

In the present embodiment, the user selects ranges to be displayed in S22, however, other configurations may be employed. The processor 202 may determine ranges to be displayed. For example, the processor 202 may acquire plural pieces of data on an eye in normal condition (i.e., normal eye) and determine a threshold based on the plural pieces of data on the normal eye. Specifically, the processor 202 may determine a threshold based on a standard deviation of the plural pieces of data on the normal eye (e.g., average ±1σ to ±3σ). The threshold may be a value that has been proven to be associated with abnormality from clinical findings. For example, a value based on which it is determined that a person has poor eyesight, a value that has been proven to be useful to detect a rupture of RPE cell, etc. can be used as the threshold. Ranges determined by the processor 202 may be presented and the user may change the presented ranges.

In the present embodiment, tomographic images showing ranges selected in S22 are superimposed and displayed in S24. However, for example, transmissibility of each tomographic image may be selectable in addition to the ranges. For example, when the entropy tomographic image is to be superimposed on top of the normal tomographic image, the processor 202 may determine whether transmissibility is selected for the entropy tomographic image, which is the upper image in the positional relationship with the normal tomographic image. This makes it possible to easily see the normal tomographic image, which is the lower image in the positional relationship with the entropy tomographic image, through the entropy tomographic image superimposed thereon. Thus, even when at least two tomographic images are superimposed on each other, the user can see both the lower tomographic image and the upper tomographic image. The transmissibility may be changeable after tomographic images have been superimposed and displayed.

In the present embodiment, images selected in S18 are superimposed. However, instead of the user selecting images to be superimposed, the same types of images as those the user previously selected may be selected, for example. Specifically, types of images selected in S18 may be stored in a memory (not illustrated), and the same types of images as those stored in the memory may be selected in S18 when the process of superimposing and displaying tomographic images is executed next time or later. Further, the superimposing order selected in S20 and the ranges selected in S22 may be stored in the memory, and the superimposing order and the ranges stored in the memory may be selected when the process of superimposing and displaying tomographic images is executed next time or later. For the colors used in tomographic images and transmissibility as well, colors and transmissibility that were selected by the user in the past may be read out from the memory and selected.

Second Embodiment

In the first embodiment, plural tomographic images are superimposed and displayed, however, other configurations may be employed. For example, en-face images may be superimposed and displayed. An en-face image is an image in which three-dimensional data is compressed into a two-dimensional frontal image by calculating the maximal value, minimal value, or average value for each A-scan regarding the three-dimensional data. Referring to FIGS. 14 to 17, a process for displaying en-face images of the subject eye 500 such that they are superimposed on each other will be described.

Figure 14:
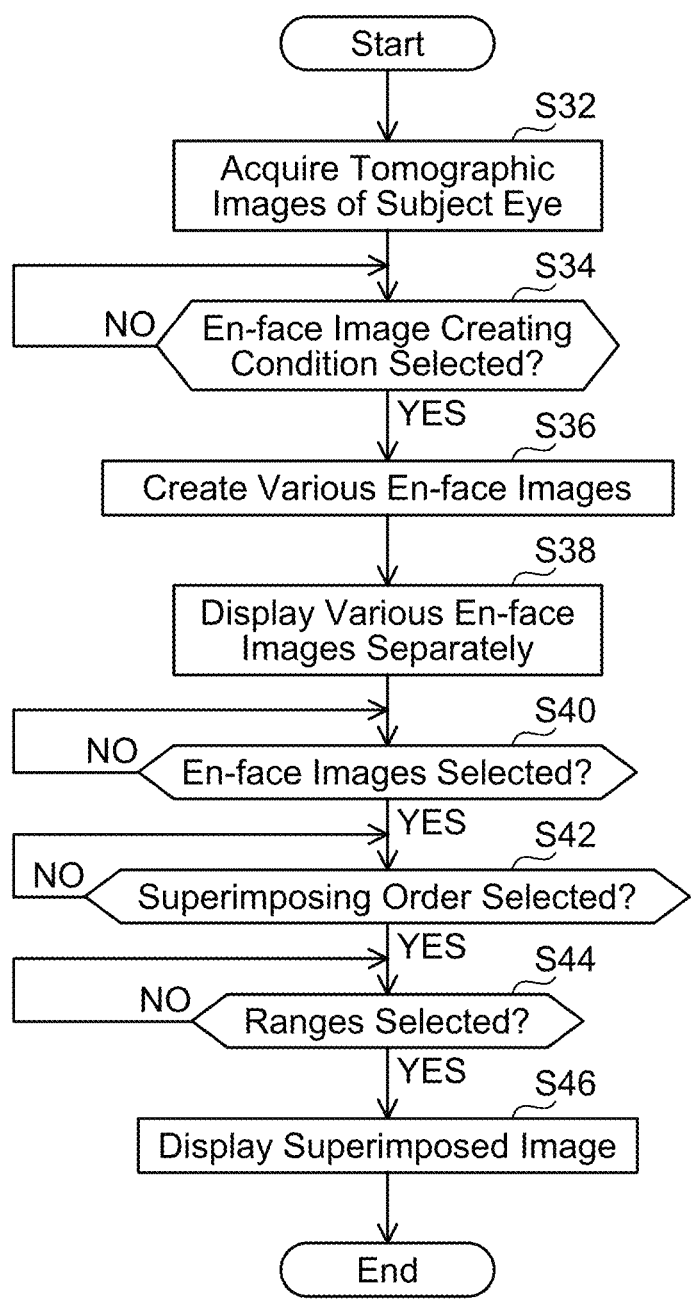
FIG. 14 is a flowchart illustrating an example of a process for displaying en-face images of a subject eye such that they are superimposed on each other.

To create en-face images, the user inputs an instruction to create en-face images by using the input device (not illustrated) such as a mouse, etc. A process for creating the en-face images is thereby started. Then, as illustrated in FIG. 14, the processor 202 first acquires tomographic images of the subject eye 500 (S32). A detailed description for a process of S32 is omitted because the process is similar to the process of S12 in the first embodiment. The instruction to create the en-face images may be inputted after the process of S32.

Then, the processor 202 determines whether an en-face image creating condition is selected (S34). Specifically, the user selects a depthwise area for the en-face images to be created. Further, the user selects which of the maximal value, minimal value, or average value should be calculated to create the en-face images.

Here, how a depthwise area for the en-face images to be created is selected will be described. As the depthwise area for the en-face images to be created, the entire depthwise area or a specific depthwise area of the tomographic images of the subject eye 500 acquired in S32 can be selected. In a case of creating the en-face images for a specific depthwise area of the tomographic images of the subject eye 500, they are created as follows. The processor 202 first specifies boundaries in the subject eye 500 (segments the subject eye 500) on each tomographic image. A detailed description for this segmentation is omitted because it can be performed using known methods. Then, the user selects a depthwise area. For example, the user selects two boundaries between desired segmented layers. In this case, the processor 202 creates the en-face images only for an area between the two selected layer boundaries. The user may select one layer boundary and a thickness for the en-face images to be created. In this case, the processor 202 creates the en-face images for the selected thickness from the selected layer boundary. The depthwise area may be changeable after it has been selected by the user. For example, the depthwise area may be shifted in the depth direction while the thickness selected by the user is maintained.

In S34, the user selects the entire depthwise area or a specific depthwise area for the en-face images to be created, using the input device such as a mouse, etc. In case of selecting a specific depthwise area as the depthwise area for the en-face images to be created, the user further selects two boundaries of segmented layers or one boundary of segmented layers. Further, the user selects which of the maximal value, minimal value, or average value should be used to create the en-face images. The processor 202 waits until the completion of the selection of en-face image creating condition is notified (NO in S34).

When the completion of the selection of the en-face image creating condition has been notified (YES in S34), the processor 202 creates various types of en-face images showing different characteristics from the tomographic images acquired in S32 based on the creating condition selected in S34 (S36). That is, an en-face image is created for each of images showing characteristics (e.g., an image showing a tissue in the subject eye 500 by scattering intensity, an image showing entropy in the subject eye 500, an image showing birefringence in the subject eye 500, an image showing a fiber direction in the subject eye 500, and an image showing a blood flow in the subject eye 500). Then, the processor 202 displays the various en-face images created in S36 on the monitor 120 (S38). The processor 202 then determines whether images are selected from among the en-face images displayed on the monitor 120 (S40), determines whether a superimposing order of the selected en-face images is selected (S42), and determines whether ranges to be displayed are selected for the en-face images (S44). Then, the processor 202 displays the en-face images on the monitor 120 such that they are superimposed on each other based on the information selected in S40 to S44 (S46). A detailed description for processes of S44 to S44 is omitted because they are similar to the processes of S18 to S22 in the first embodiment. In the present embodiment as well, the superimposing order, the ranges to be displayed, and transmissibility may be changeable after the en-face images have been superimposed and displayed. Further, the en-face image creating condition in S34 may be also changeable after the en-face images have been superimposed and displayed. Displaying the en-face images such that they are superimposed on each other makes it possible to easily check the subject eye 500 over a wider range.

Figure 15A:
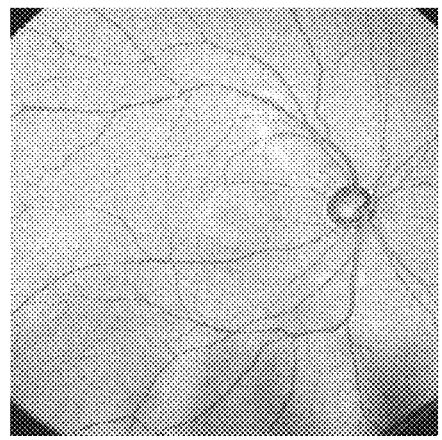
FIG. 15A is a normal en-face image of a subject eye.
Figure 15B:
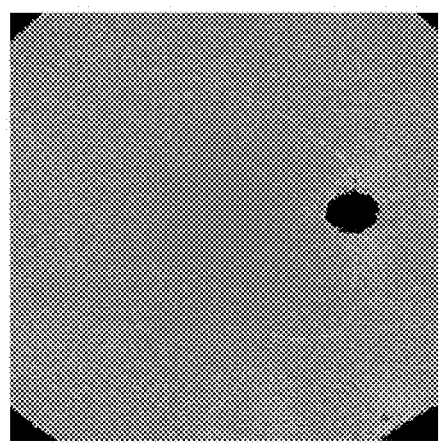
FIG. 15B is an en-face image showing entropy in the subject eye.
Figure 15C:
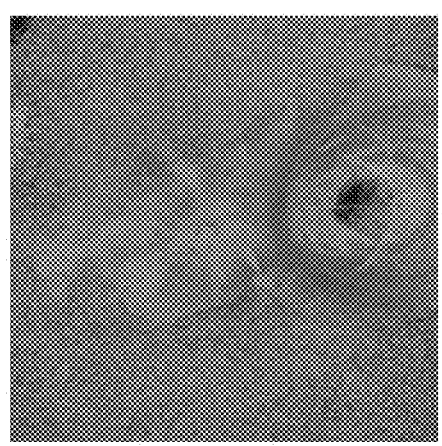
FIG. 15C is an en-face image showing birefringence in the subject eye.

FIGS. 15A to 15C and 16A to 16D illustrate examples of en-face images created by calculating the maximal value of the entire depthwise area of tomographic images of the subject eye 500. FIG. 15A illustrates an en-face image created from a normal tomographic image (which may be termed "normal en-face image"), FIG. 15B illustrates an en-face image created from an entropy tomographic image (which may be termed "entropy en-face image"), and FIG. 15C illustrates an en-face image created from a birefringence tomographic image (which may be termed "birefringence en-face image").

Figure 16A:
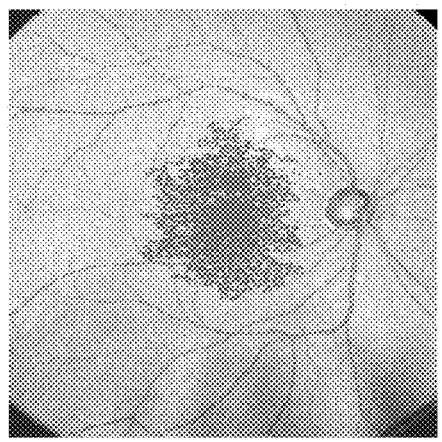
FIG. 16A is an image in which the en-face image showing entropy in the subject eye is superimposed on the normal en-face image.

FIGS. 16A to 16D illustrate examples of how the en-face images of FIGS. 15A to 15C are superimposed and displayed. FIG. 16A illustrates an image in which the entropy en-face image is superimposed on top of the normal en-face image. For the normal en-face image, the entire range is selected, while for the entropy en-face image, a range of 0.4 to 0.5 is selected. Displaying the entropy en-face image and the normal en-face image such that the entropy en-face image is superimposed on top of the normal en-face image helps to grasp how melanin distributes over a wider area of the subject eye 500, and thus facilitates the understanding of melanin distribution over an entire fundus surface of the subject eye 500.

Figure 16B:
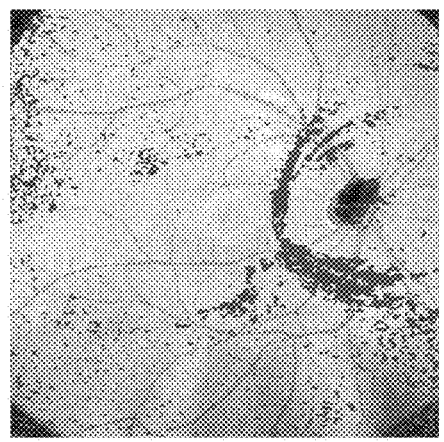
FIG. 16B is an image in which the en-face image showing birefringence in the subject eye is superimposed on the normal en-face image.

FIG. 16B illustrates an image in which the birefringence en-face image is superimposed on top of the normal en-face image. For the normal en-face image, the entire range is selected, while for the birefringence en-face image, a range of 0.3 to 0.5 rad is selected. Displaying the birefringence en-face image and the normal en-face image such that the birefringence en-face image is superimposed on top of the normal en-face image facilitates the understanding of fiber density distribution over the entire fundus surface of the subject eye 500.

Figure 16C:
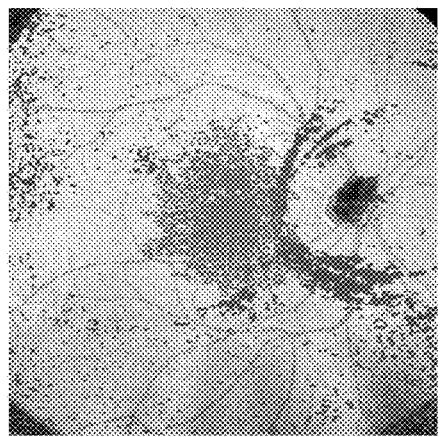
FIG. 16C is an image in which the en-face image showing birefringence in the subject eye is superimposed on the normal en-face image and the en-face image showing entropy in the subject eye is further superimposed on the en-face image showing birefringence in the subject eye.
Figure 16D:
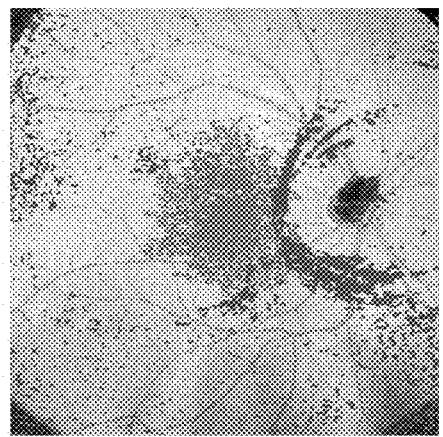
FIG. 16D is an image in which the en-face image showing entropy in the subject eye is superimposed on the normal en-face image and the en-face image showing birefringence in the subject eye is further superimposed on the en-face image showing entropy in the subject eye.

FIG. 16C illustrates an image in which the birefringence en-face image is superimposed on top of the normal en-face image and the entropy en-face image is superimposed on top of the birefringence en-face image. FIG. 16D illustrates an image in which the entropy en-face image is superimposed on top of the normal en-face image and the birefringence en-face image is superimposed on top of the entropy en-face image. As illustrated in FIGS. 16C and 16D, displaying the normal en-face image, the entropy en-face image, and the birefringence en-face image such that the entropy en-face image and the birefringence en-face image are superimposed on the normal en-face image facilitates the understanding of the correspondence relationship between melanin distribution and fiber density distribution over the entire fundus surface of the subject eye 500.

Figure 17C:
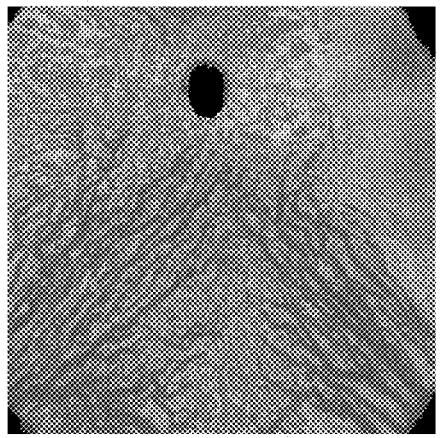
FIG. 17C is an image in which the image of FIG. 17B is superimposed on the image of FIG. 17A.
Figure 17F:
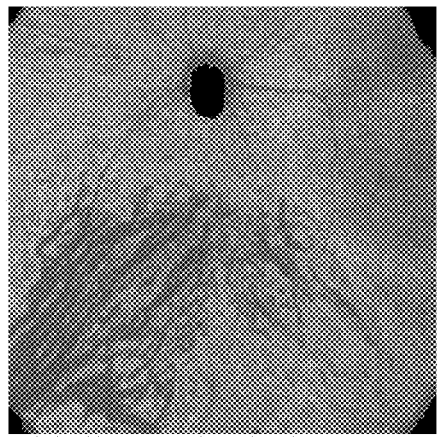
FIG. 17F is an image in which the image of FIG. 17E is superimposed on the image of FIG. 17D.
Figure 17B:
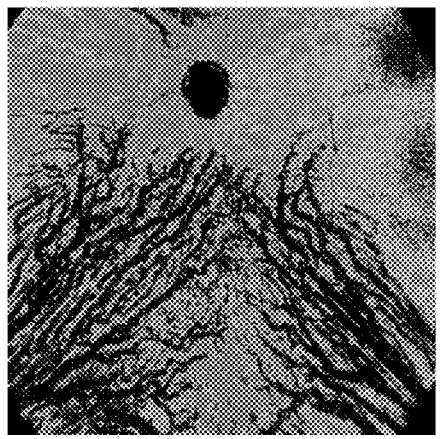
FIG. 17B is an example of an en-face image created by selecting a depthwise area and is an en-face image showing entropy near the choroidal superficial layer in the subject eye.
Figure 17E:
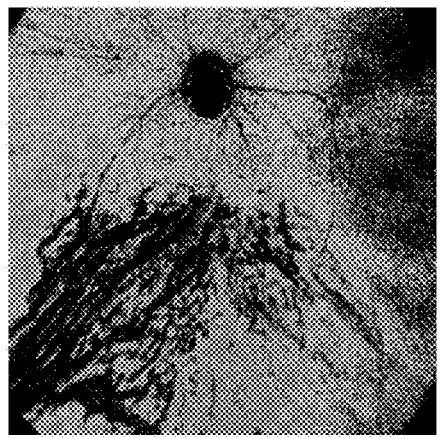
FIG. 17E is an example of an en-face image created by selecting a depthwise area and is an en-face image showing entropy near the choroid deep layer in the subject eye.
Figure 17A:
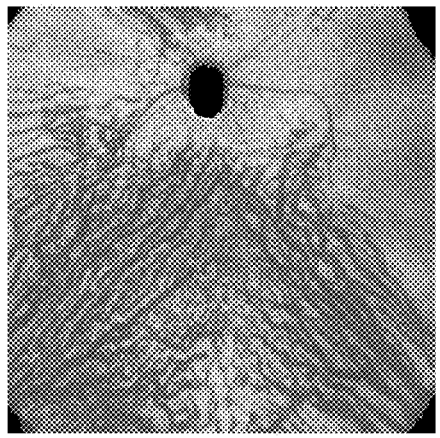
FIG. 17A is an example of an en-face image created by selecting a depthwise area and is a normal en-face image near a choroidal superficial layer in a subject eye.
Figure 17D:
FIG. 17D is an example of an en-face image created by selecting a depthwise area and is a normal en-face image near a choroid deep layer in the subject eye.

FIGS. 17A to 17F illustrate examples of en-face images created by calculating the maximal value of a specific depthwise area of tomographic images of the subject eye 500. FIG. 17A illustrates a normal en-face image with an area around the choroidal superficial layer selected, and FIG. 17B illustrates an entropy en-face image with the same area as the one in FIG. 17A (i.e., the area around the choroidal superficial layer) selected. FIG. 17C illustrates an image in which the entropy en-face image of FIG. 17B with only a range of 0.2 to 0.5 is superimposed on top of the normal en-face image of FIG. 17A. FIG. 17D illustrates a normal en-face image with an area around the choroid deep layer selected, and FIG. 17E illustrates an entropy en-face image with the same area as the one in FIG. 17D (i.e., the area around the choroid deep layer) selected. FIG. 17F illustrates an image in which the entropy en-face image of FIG. 17E with only a range of 0.2 to 0.5 is superimposed on top of the normal en-face image of FIG. 17D. As illustrated in FIGS. 17C and 17F, creating en-face images by selecting a depthwise area of the subject eye 500 helps to understand the condition of the subject eye 500 in the user-desired specific area (tissue or layer). This more efficiently helps diagnosis for ailments of the subject eye 500.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed. Further, the purpose of the examples illustrated by the present description or drawings is to satisfy multiple objectives simultaneously, and satisfying any one of those objectives gives technical utility to the present disclosure.

What is claimed is:

1. An optical coherence tomographic device of polarization-sensitive type, comprising:
an image capturing unit configured to capture a tomographic image of a subject eye; and
a display unit configured to display the tomographic image captured by the image capturing unit,
wherein
the tomographic image comprises at least two images selected from a group consisting of: an image showing a tissue in the subject eye by scattering intensity, an image showing a melanin distribution in the subject eye, an image showing a fiber density in the subject eye, an image showing a fiber direction in the subject eye, and an image showing a blood flow in the subject eye, and
the display unit is configured to display the at least two images at a same position and on a same cross section such that the at least two images are superimposed on each other.

2. The optical coherence tomographic device according to claim 1, further comprising an input device for input of a numerical range of an index to be displayed for each of the at least two images,
wherein the display unit is configured to display each of the at least two images according to the numerical range inputted through the input device.

3. The optical coherence tomographic device according to claim 2, wherein
the input device is further for input of an order in which the at least two images are superimposed, and
the display unit is configured to display the at least two images such that the at least two images are superimposed on each other in the order inputted through the input device.

4. The optical coherence tomographic device according to claim 1, wherein
the image showing the melanin distribution in the subject eye is created based on entropy, and
the image showing a fiber density in the subject eye is created based on birefringence.

5. The optical coherence tomographic device according to claim 1, wherein
the image capturing unit comprises:
a light source;
a measurement optical system configured to generate measurement light from light outputted from the light source and to generate reflected light from the subject eye by irradiating the subject eye with the generated measurement light;
a reference optical system configured to generate reference light from the light outputted from the light source; and
an interference light detector configured to detect interference light, the interference light being a combination of the reflected light from the subject eye generated by the measurement optical system and the reference light generated by the reference optical system,
the measurement optical system is configured to:
generate first polarization measurement light and second polarization measurement light from the light outputted from the light source, wherein the first polarization measurement light vibrates in a first direction and the second polarization measurement light vibrates in a second direction different from the first direction;
irradiate the subject eye with the first polarization measurement light and the second polarization measurement light;
generate first polarization reflected light and second polarization reflected light from reflected light of the first polarization measurement light from the subject eye, wherein the first polarization reflected light vibrates in the first direction and the second polarization reflected light vibrates in the second direction; and
generate third polarization reflected light and fourth polarization reflected light from reflected light of the second polarization measurement light from the subject eye, wherein the third polarization reflected light vibrates in the first direction and the fourth polarization reflected light vibrates in the second direction, and
the interference light detector is configured to detect first interference light, second interference light, third interference light, and fourth interference light, wherein the first interference light is a combination of the first polarization reflected light and the reference light, the second interference light is a combination of the second polarization reflected light and the reference light, the third interference light is a combination of the third polarization reflected light and the reference light, and the fourth interference light is a combination of the fourth polarization reflected light and the reference light.

6. The optical coherence tomographic device according to claim 5, wherein
the image showing a tissue in the subject eye by scattering intensity is created by using at least one of the first interference light, the second interference light, the third interference light, and the fourth interference light,
each of the image showing a melanin distribution in the subject eye, the image showing a fiber density in the subject eye, the image showing a fiber direction in the subject eye, and the image showing a blood flow in the subject eye is created by using the first interference light, the second interference light, the third interference light, and the fourth interference light.

7. The optical coherence tomographic device according to claim 1, wherein
the display unit is configured to display en-face images of the at least two images created from the tomographic image captured by the image capturing unit, and
the display unit is configured to display the en-face images of the at least two images such that the en-face images are superimposed on each other.

8. A non-transitory computer-readable recording medium storing computer-readable instructions for an optical coherence tomographic device,
wherein the computer-readable instructions, when executed by a processor of the optical coherence tomographic device, cause the optical coherence tomographic device to:
create at least two tomographic images selected from a group consisting of: a tomographic image showing a tissue in the subject eye by scattering intensity, a tomographic image showing a melanin distribution in the subject eye, a tomographic image showing a fiber density in the subject eye, a tomographic image showing a fiber direction in the subject eye, and a tomographic image showing a blood flow in the subject eye; and display the at least two tomographic images at a same position and on a same cross section such that the at least two tomographic images are superimposed on each other.

\* \* \* \* \*